United States Patent [19]

Neef et al.

[11] Patent Number: 5,292,728
[45] Date of Patent: Mar. 8, 1994

[54] 24-OXA DERIVATIVES IN THE VITAMIN D SERIES

[75] Inventors: Gunter Neef; Gerald Kirsch; Andreas Steinmeyer; Katica Schwarz; Matthias Brautigam; R. Thieroff-Ekerdt; Petra Rach, all of Berlin, Fed. Rep. of Germany

[73] Assignee: Schering Aktiengesellschaft, Berlin und Bergkamen, Fed. Rep. of Germany

[21] Appl. No.: 938,175

[22] Filed: Dec. 4, 1992

[30] Foreign Application Priority Data

Apr. 6, 1990 [DE] Fed. Rep. of Germany ....... 4011682

[51] Int. Cl.$^5$ .................... A61K 31/59; C07C 401/00
[52] U.S. Cl. .................................. 514/167; 552/653
[58] Field of Search .................. 552/653; 514/167

[56] References Cited

U.S. PATENT DOCUMENTS 4,125,544 11/1978 Dygos .............................. 260/397.4

FOREIGN PATENT DOCUMENTS 184112 6/1986 European Pat. Off. ... C07C 172/00
9009991 9/1990 World Int. Prop. O. ... C07C 401/00

OTHER PUBLICATIONS

Derwent Abstract, vol. 10 (335) (C-384) (2391), Nov. 13, 1986.

*Primary Examiner*—Marianne M. Cintins
*Assistant Examiner*—Kimberly J. Kestler
*Attorney, Agent, or Firm*—Millen, White, Zelano, Branigan

[57] ABSTRACT

New 24-oxa derivatives in the vitamin D series of general formula I are described

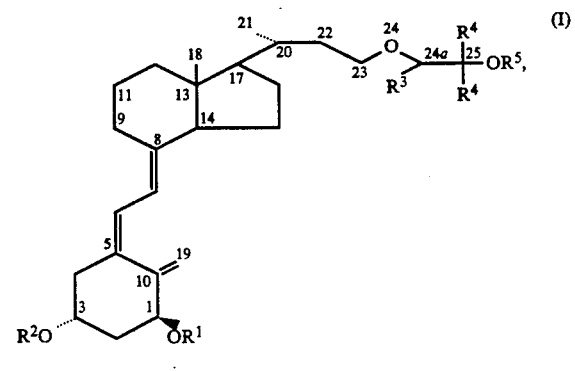

in which
$R^1$, $R^2$ and $R^5$, independently of one another, mean a hydrogen atom or an acyl group with 1 to 9 carbon atoms,
$R^3$ means a hydrogen atom or a linear or branched alkyl group with 1 to 4 carbon atoms and
$R^4$ means a hydrogen atom each or a linear or branched alkyl group each with 1 to 4 carbon atoms.

Pharmaceutical preparations which contain these compounds are also disclosed.

7 Claims, No Drawings

24-OXA DERIVATIVES IN THE VITAMIN D SERIES

This invention relates to 24-oxa derivatives in the vitamin D series of general formula I

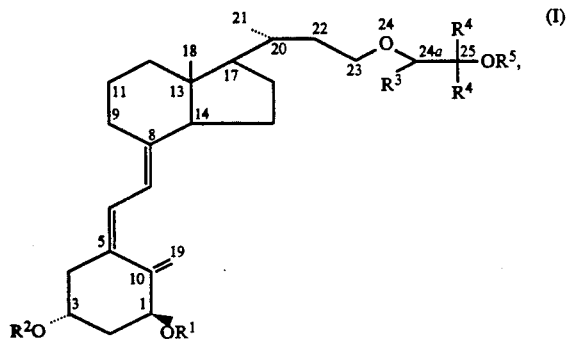

in which
R$^1$, R$^2$ and R$^5$, independently of one another, mean a hydrogen atom or an acyl group with 1 to 9 carbon atoms,
R$^3$ means a hydrogen atom or a linear or branched alkyl group with 1 to 4 carbon atoms and
R$^4$ means a hydrogen atom each or a linear or branched alkyl group each with 1 to 4 carbon atoms,
a process for their production, pharmaceutical preparations which contain these compounds as well as their use for the production of pharmaceutical agents. The acyl groups with 1 to 9 carbon atoms possible for the radicals R$^1$, R$^2$ and R$^5$ are derived especially from saturated carboxylic acids or else from benzoic acid. Other suitable acyl radicals R$^1$, R$^2$, R$^5$ include those that are cyclic, acyclic, carbocyclic or heterocyclic—all optionally also unsaturated. The preferred radicals are derived from C$_1$ to C$_9$, especially C$_2$ to C$_5$, alkane carboxylic acids, such as, for example, acetyl—, propionyl—, butyryl—.

In alkyl groups R$^3$ and R$^4$, which can be straight-chain or branched, suitable in the first place are the methyl, ethyl, propyl group and for R$^3$ additionally the isopropyl group and for R$^4$ additionally the n-butyl group. R$^3$ and R$^4$ can be identical or different.

Especially preferred according to this invention are the following compounds:
1α,25-dihydroxy-24-oxa-24-homo-cholecalciferol
1α,25-dihydroxy-26,27-dimethyl-24-oxa-24-homo-cholecalciferol
26,27-diethyl-α,25-dihydroxy-24-oxa-24-homo-cholecalciferol
1α,25-dihydroxy-24-oxa-26,27-di-n-propyl-24-homo-cholecalciferol
1α,26-dihydroxy-24-oxa-cholecalciferol
1α,26-dihydroxy-27 -methyl-24-oxa-cholecalciferol.

Natural vitamins D$_2$ and D$_3$ (cf. general formula A) are biologically inactive in themselves and are converted into their biologically active metabolites only after hydroxylation in 25-position in the liver or in 1-position in the kidney. The action of vitamins D$_2$ and D$_3$ consists in the stabilization of the plasma Ca$^{++}$ and the plasma phosphate level; they counteract a reduction of the plasma Ca$^{++}$ level.

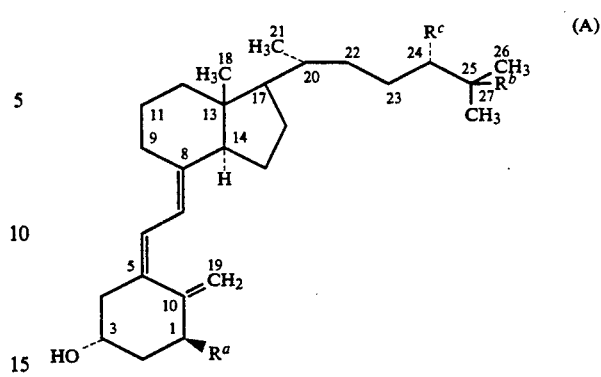

ergocalciferol: R$^a$=R$^b$=H, R$^c$=CH$_3$, vitamin D$_2$ double bond C-22/23
cholecalciferol: R$^a$=R$^b$=R$^c$=H, vitamin D$_3$
25-hydroxycholecalciferol: R$^a$=R$^c$=H, R$^b$=OH
1α-hydroxycholecalciferol: R$^a$=OH, R$^b$=R$^c$=H
1α,25-dihydroxycholecalciferol: R$^a$=R$^b$=OH, R$^c$=H calcitriol Besides their marked effect on the calcium and phosphate metabolism, vitamins D$_2$ and D$_3$ and their synthetic derivatives also have proliferation-inhibiting and cell-differentiating actions (H. F. De Luca, The Metabolism and Function of Vitamin D in Biochemistry of Steroid Hormones, publisher H. L. J. Makin, 2nd edition, Blackwell Scientific Publications 1984, pp. 71-116). But overdosage phenomena can occur with the use of vitamin D (hypercalcemia).

Besides the compounds according to the invention, there is already a series of oxa derivatives in the vitamin D series. There have been described 20-oxa, 22-oxa and 23-oxa analogs of calcitriol (23-oxa: U.S. Pat. No. 4 772 433, Inv. R. Hesse, 1988; 22-oxa: E. Murayama et al., Chem. Pharm. Bull. 34,4410, 1987; 20-oxa: J. Abe et al., FEBS Lett. 222, 58, 1987). One 24-oxa analog of calcitriol is chemically not reproducible, since by its nature as an open-chain hemiacetal, it would immediately be decomposed in aqueous medium.

As DeLuca et al. (Proc. Natl. Acad. Sci. USA 84, 2610, 1987) could show, also 24-homo derivatives of calcitriol exhibit a great affinity to the calcitriol receptor.

A part of the compounds according to the invention, which have to be classified as 24-oxa-24-homo analogs of the calcitriol, thus represent a novel combination of known structure features increasing effectiveness.

It has now been found that the 24-oxa vitamin D derivatives of general formula I according to the invention are distinguished by great affinity for the calcitriol receptor and also in high dosage do not cause any increase of the calcium level in the plasma. But the proliferation-inhibiting properties of the calcitriol are not reduced (dissociation).

The vitamin D activity of the compounds according to the invention is determined by the calcitriol receptor test. It is performed by using a specific receptor protein from the intestine of rachitic chickens. Receptor-containing binding protein is incubated with $^3$H calcitriol (0.5 ng/ml) in a reaction volume of 0.575 ml in the absence and in the presence of the test substances for one hour in a test tube. For separation of free and receptor-bound calcitriol, a charcoal-dextran absorption is performed. For this purpose, 200 μl of a charcoal-dextran suspension is placed in each test tube and incubated at 22° C. for 30 minutes. Then, the samples are centrifuged at 1500×g for 10 minutes at 4° C. The supernatant is decanted and after 1-hour equilibrating in Atom-Light is measured in a β-counter.

The competition curves obtained with different concentrations of the test substance as well as of the reference substance (unmarked calcitriol) for the displacement of $^3$H-labeled reference substance ($^3$H calcitriol) are put in relation to one another and a competition factor (CF) is obtained.

There is defined as quotient from the concentrations of the respective test substance and the reference substance, which are necessary for 50% competition:

$$CF = \frac{\text{concentration of test substance at 50\% competition}}{\text{concentration of reference substance at 50\% competition}}$$

Accordingly, 1α,25-dihydroxy-26,27-dimethyl-24-oxa-24-homo-cholecalciferol has a CF value of 3 and 1α,25-dihydroxy-24-oxa-24-homo-cholecalciferol has a CF value of 7.

By the greatly reduced hypercalcemia risk, the substances according to the invention are especially suitable for the production of pharmaceutical agents for the treatment of diseases which are characterized by a hyperproliferation, e.g., hyperproliferative diseases of the skin (psoriasis) and malignant tumors (leukemia, colon carcinoma, breast carcinoma). In an especially preferred embodiment of the invention, calcitriol receptors are detected in the target organ before the treatment.

This invention thus relates to pharmaceutical preparations, which contain at least one compound according to general formula I together with a pharmaceutically compatible vehicle.

The compounds can be formulated as solutions in pharmaceutically compatible solvents or as emulsions, suspensions or dispersions in suitable pharmaceutical solvents or vehicles or as pills, tablets or capsules, which contain solid vehicles in a way known in the art. For a topical use, the compounds are advantageously formulated as creams or ointments or in a similar pharmaceutical agent form suitable for topical use. Each such formulation can contain another pharmaceutically compatible and nontoxic auxiliary agent, such as, e.g., stabilizers, antioxidizing agents, binding agents, dyes, emulsifiers or taste corrigents. The compounds are advantageously administered by injection or intravenous infusion of suitable sterile solutions or as oral doses by alimentary tract or topically in the form of creams, ointments, lotions or suitable transdermal patches, as is described in EP-A-0387 077.

The daily dose is about 0.1 μg/patient/day—1000 μg (1 mg)/patient/day,
preferably 1.0 μg/patient/day—500 μg/patient/day.

The compounds according to the invention are generally administered analogously to the administration of the known agent "calcipotriol" for treatment of psoriasis.

Moreover, the invention relates to the use of the compounds according to formula I for the production of pharmaceutical agents.

The production of 24-oxa vitamin D derivatives of formula I takes place according to the invention in that a compound of general formula II

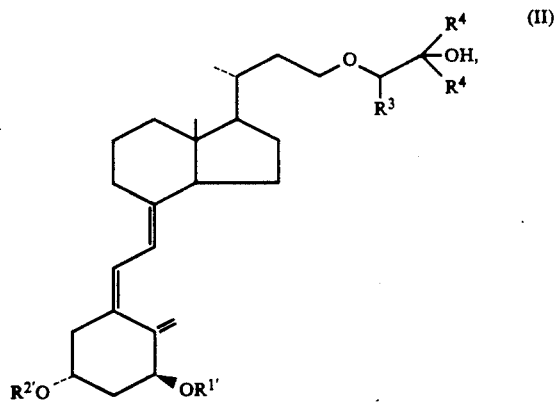

in which
R$^{1'}$ and R$^{2'}$ stand for hydroxy protecting groups and R$^3$ and R$^4$ have the meaning indicated in formula I, by cleavage of these hydroxy protecting groups is converted into the free trihydroxy compound (compound of general formula I, in which R$^1$=R$^2$=R$^5$=H) and optionally the latter by partial or complete esterification of the free hydroxy groups into the corresponding acyl compound (compound of general formula I, in which R$^1$ and-/or R$^2$ and/or R$^5$ means/mean a C$_1$-C$_9$ acyl group).

As hydroxy protecting groups R$^{1'}$ and R$^{2'}$ primarily tertiary silyl groups, for example the trimethylsilyl radical or the tert-butyl-dimethylsilyl radical, are suitable. Their cleavage is possible, e.g., by use of tetra-n-butyl ammonium fluoride.

After the protecting group cleavage, free hydroxy groups optionally can be esterified. The esterification of the different free hydroxy groups can take place according to common processes partially or completely with the appropriate carboxylic acid halide (halide=-chloride, bromide) or carboxylic acid anhydride.

It is also possible to esterify a tertiary 25-hydroxy group even before the protecting group cleavage or before the photoisomerization.

As initial material for the production of the initial compounds of general formula II to be used according to the invention, alcohols of general formula III are used

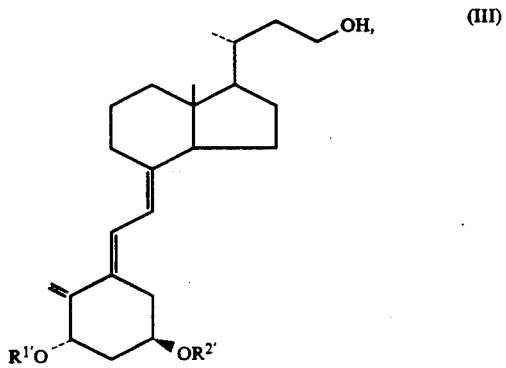

in which
R$^{1'}$ and R$^{2'}$ have the meaning already indicated.
1S,3R-bis-(tert-Butyldimethylsilyloxy)-24-nor-9,10-secochola-5E,7E,10(19)-trien-23-ol can be produced, e.g., according to U.S. Pat. No. 4,512,925 (inv.: DeLuca et al., 1985).

By reaction of a compound of general formula III with bromoacetic acid tert-butyl ester in the two-phase system, toluene/25% sodium hydroxide solution in the presence of a phase transfer catalyst (in the framework of this invention, tetra-n-butyl-ammonium hydrogen sulfate or fluoride is used), the esters of formula IV are obtained in high yield

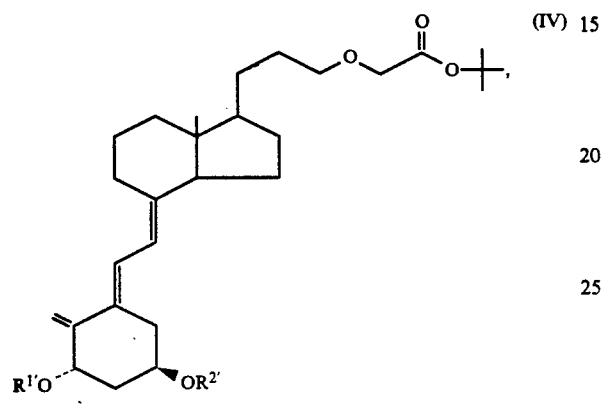

If end products of general formula I are desired in which $R^3$ means an alkyl group with 1 to 4 carbon atoms, first intermediate stage IV is alkylated in the presence of a strong base such as, for example, lithium diisopropylamide in an aprotic solvent such as tetrahydrofuran with an alkyl halide of general type $R^3$Hal ($R^3=C_1-C_4$ alkyl, Hal=Br, I) on the methylene group adjacent to the carbonyl group.

The resulting compounds of general formula V

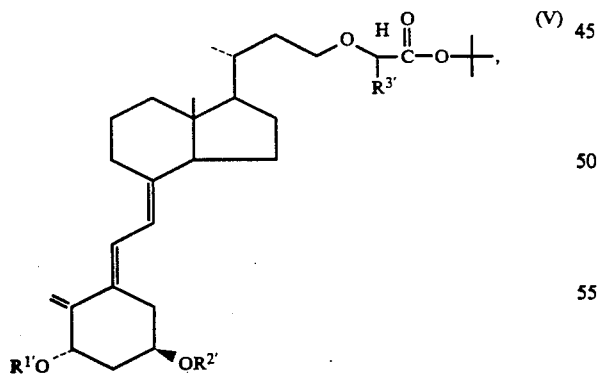

are generally obtained as diastereomeric mixtures and are used without separation in the following reactions.

This intermediate stage IV can be converted with Grignard reagents of general formula $R^4$MgX ($R^4=C_1-C_4$ alkyl, X=Cl, Br, I) in an excess of 2 to 10 mole equivalents to the intermediate products of general formula IV

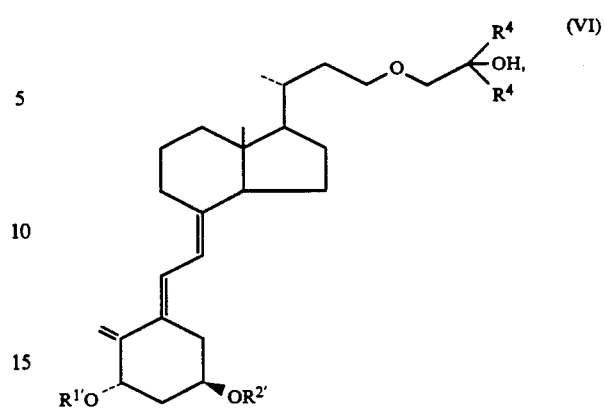

The reduction of the ester group in the compounds of formula IV or formula V leads to the compounds of general formula VII

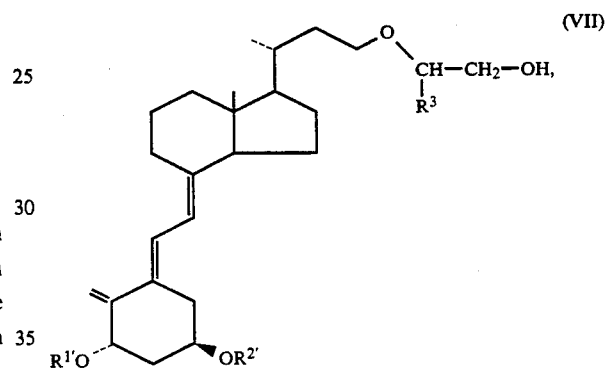

in which $R^3$ means a hydrogen atom or a linear or branched $C_1-C_4$ alkyl group and $R^{1'}$ and $R^{2'}$ have the above-indicated meaning.

After standard processes of the vitamin D chemistry by radiation with ultraviolet light in the presence of a so-called "Triplett sensitizer" (in the framework of this invention, anthracene is used for this purpose), then the compounds of general formulas VI and VII can be converted into compounds of general formula II. By cleavage of the pi bond of the 5,6-double bond, rotation of the A ring by 180° around the 5,6-single bond and reestablishment of the 5,6-double bond, the stereoisomerism on the 5,6-double bond is reversed.

The key step to the synthesis of the initial compounds of general formula II is the reaction of alcohol II with bromoacetic acid tert-butyl ester under phase transfer conditions. It is known to one skilled in the art that the corresponding reactions with bromoacetic acid methyl-(ethyl) ester take place extremely unsatisfactorily, since essentially only transesterification and not formation of the desired etherification products results.

Further the fact is surprising that tert-butyl ester IV can be reacted with alkyl Grignard reagents without problem, although the steric hindrance by the tert-butyl group had led to the expectation of a considerably reduced reactivity.

The following examples serve for a more detailed explanation of the invention.

EXAMPLE 1

1α,25-Dihydroxy-26,27-dimethyl-24-oxa-24-homo-cholecalciferol a) A solution of 1S,3R-bis-(tert-butyldimethylsilyloxy)-24-nor-9,10-secochola-5E,7E,10(19)-trien-23-ol in 14 ml of toluene, after addition of 1.49 ml of bromoacetic acid tert-butyl ester and 5.5 ml of 25% sodium hydroxide solution and 26.6 mg of tetra-n-butyl ammonium hydrogen sulfate, is stirred for 24 hours at room temperature. Then 30 mg of tetrabutyl ammonium salt is again added and stirred for another 24 hours at 25° C. For working up, it is diluted with diethyl ether, washed with water and saturated common salt solution, the ether phase is dried on $Na_2SO_4$ and concentrated by evaporation. The crude product is gradient chromatographed on 160 g of silica gel with hexane/ethyl acetate (0–5%) 1.15 g of 1S,3R—bis-(tert-butyldimethylsilyloxy)-25-(tert-butylcarbonyloxy)-24-oxa-26,27-dinor-9,10-secocholesta-5E,7E,10(19)-triene is obtained as colorless oil.

b) From 297 mg of magnesium (chips) and 0.91 ml of bromoethane in 7 ml of tetrahydrofuran, ethyl magnesium bromide is produced in the usual way and a solution of 750 mg of the oxa ester, obtained under a), in 10 ml of absolute THF is instilled at room temperature. After addition, it is stirred for 1.5 hours at 25° C., poured in water and extracted with ethyl acetate. Chromatography of the crude product on silica gel with hexane/ethyl acetate produces 520 mg of 1S,3R-bis-(tert-butyldimethylsilyloxy)-26,27-dimethyl-24-oxa-24-homo-9,10-secocholesta-5E,7E,10(19)-trien-25-ol as colorless oil.

$^1$H-NMR (CDCl$_3$): δ=0.54 ppm(s,3H,H-18); 3.37(AB-qu.,J=10,5 Hz,2H,OCH$_2$); 3.48(m,2H,CH$_2$O); 4.22 (m,1H,H-3); 4.53(m,1H,H-1); 4.93 and 4.98 (m; 1H,H-19 each); 5.82 and 6.46 (d, J=11 Hz; 1H,H-6,H-7 each).

c) A solution of 500 mg of the product, obtained under b), in 90 ml of toluene, after addition of 88 mg of anthracene and 0.05 ml of triethylamine, is irradiated for 18 minutes at room temperature in an immersion apparatus (Pyrex glass) with a mercury high-pressure lamp (Heraeus TQ 150). After concentration by evaporation of the reaction solution, the residue is chromatographed on silica gel with hexane/ethyl acetate. 490 mg of 1S,3R-bis-(tert-butyldimethylsilyloxy)-26,27-dimethyl-24-oxa-24-homo-9,10-secocholesta-5Z,7E-10(19)-trien-25-ol is obtained as colorless oil.

d) A solution of 480 mg of the product, obtained under c), in 15 ml of THF, after addition of 3 ml of a 1-molar solution of tetra-n-butyl ammonium fluoride in THF, is stirred for 60 minutes at 50° C. After cooling, it is diluted with ethyl acetate, washed with NaHCO$_3$ solution and water, dried on Na$_2$SO$_4$ and concentrated by evaporation. Chromatography of the crude product on silica gel with hexane/ethyl acetate yields 200 mg of 1α,25-dihydroxy-26,27-dimethyl-24-oxa-24-homo-cholecalciferol as amorphous solid.

$^1$H-NMR (CDCl$_3$): δ=0.55 ppm(s,3H,H-18); 0.87(t,J=7 Hz, CH$_2$CH$_3$); 0.94(d,J=7 Hz,3H,H-21); 1.50(m,CH$_2$CH$_3$); 3.26(AB-qu., J=10,5 Hz,2H,CH$_2$O); 3.48(m,2H,CH$_2$); 4.22(m,1H,H-3); 4.43(m,1H,H-1); 5.00 and 5.32(m; 1H,H-19 each); 6.02 and 6.38 (d,J=11 Hz; 1H,H-6,H-7 each).

EXAMPLE 2

1α,25-Dihydroxy-24-oxa-24-homo-cholecalciferol

The production of the title compound takes place analogously to the process described in example 1. In process step 1b), only ethyl magnesium bromide is replaced by methyl magnesium bromide (1.5 molar solution in THF/toluene). The title compound is obtained as colorless oil.

$^1$H-NMR (CDCl$_3$): α=0.53 ppm(s,3H,H-18); 0.95(d,J=7 Hz,3H,H-21); 1.20(s,6H,H-26,H-27); 3.23(AB-qu.,J=10,5 Hz,2H,CH$_2$O); 3.50(m,2H,CH$_2$O); 4.23(m,1H,H-3); 4.43(m,1H,H-1); 5.00 and 5.32 (m; 1H,H-19 each); 6.02 and 6.38 (d,J=11 Hz; 1H,H-6,H-7 each).

EXAMPLE 3

1α,26-Dihydroxy-24-oxa-cholecalciferol a) A solution of 0.6 ml of diisopropylamine in 6 ml of THF is mixed by instillation at 0° C. with 2.54 ml of a 1.6-molar solution of n-butyllithium in hexane. It is stirred for 15 minutes at 0° C., then cooled to −70° C. and a solution of 1.00 g of 1S,3R-bis-(tert-butyldimethysilyloxy)-25-(tert-butylcarbonyloxy)-24-oxa-26,27-dinor-9,10-secocholesta-5E,7E,10(19)-triene (see example 1a) in 15 ml of THF is instilled. After addition, it is stirred for 60 minutes at −70° C. and then 0.36 ml of iodomethane is instilled. The reaction solution is stirred for 30 minutes at −70° C. and another 30 minutes at room temperature, poured into water and extracted with ethyl acetate. Chromatography of the crude product on silica gel with hexane/ethyl acetate yields 730 mg of 1S,3R-bis-(tert-butyldimethylsilyloxy)-25-(tert-butyl carbonyloxy)-24-oxa-27-nor-9,10-secocholesta-5E,7E,10(19)-triene as an oily mixture of the C-25 epimers.

b) The product (730 mg) obtained under a) is photoisomerized in 100 ml of toluene, 140 mg of anthracene and 0.05 ml of triethylamine under the conditions of example 1c). 610 mg of 1S,3R-bis-(tert-butyldimethylsilyloxy)-25-(tert-butyl carbonyloxy)-24-oxa-27-nor-9,10-secocholesta-5Z,7E,10(19)-triene is obtained as colorless oil.

c) 380 mg of the epimer mixture obtained under b) is dissolved in 10 ml of THF and instilled at 5° C. in a suspension of 65 mg of lithium aluminum hydride in 10 ml of THF. It is stirred for 45 minutes at 5° C., then the excess reduction agent is destroyed by careful addition of aqueous THF, it is filtered and the filtrate is concentrated by evaporation. The thus obtained crude 1S,3R-bis-(tert-butyldimethylsilyloxy)-24-oxa-9,10-secocholesta-5Z,7E,10(19)-trien-26-ol is desilylated under the conditions of example 1d) with tetra-n-butyl ammonium fluoride. After chromatographic purification, 110 mg of 1α,26-dihydroxy-24-oxa-cholecalciferol is obtained as an oily mixture of the C-25 epimers in a ratio of about 1:1.

$^1$H-NMR (CDCl$_3$): δ=0.54 ppm(s,3H,H-18); 0.96(d,J=7 Hz,3H,H-21); 1.10(2d,J=6 Hz,3H,H-27); 4.22(m,1H,H-3); 4.42(m,1H,H-1); 5.00 and 5.32(s; 1H,H-19 each); 6.00 and 6.38 (d,J=11 Hz; 1H,H-6,H-7 each).

We claim:

1. 24-Oxa derivatives in the vitamin D series of general formula I

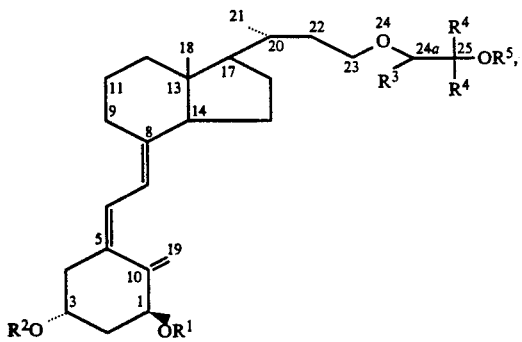

in which

R$^1$, R$^2$ and R$^5$, independently of one another, are a hydrogen atom or an acyl group with 1 to 9 carbon atoms, R$^3$ is a hydrogen atom or a linear or branched alkyl group with 1 to 4 carbon atoms and R$^4$ is a hydrogen atom or a linear or branched alkyl group having 1 to 4 carbon atoms.

2. Compounds according to claim 1, in which R$^1$, R$^2$ and R$^5$ are hydrogen atoms.

3. Compounds according to claim 1, wherein R$^3$ is a hydrogen atom.

4. Compounds according to claim 1, wherein R$^3$ is a methyl, ethyl, propyl or isopropyl group.

5. Compounds according to claim 1, wherein R$^4$ is a methyl, ethyl, propyl or butyl group.

6. A compound which is 1α,25-dihydroxy-24-oxa-24-homo-cholecalciferol,
1α,25-dihydroxy-26,27-dimethyl-24-oxa-24-homo-cholecalciferol,
26,27-diethyl-1α,25-dihydroxy-24-oxa-24-homo-cholecalciferol,
1α,25-dihydroxy-24-oxa-26,27-di-n-propyl-24-homo-cholecalciferol,
1α,26-dihydroxy-24-oxa-cholecalciferol, or
1α,26-dihydroxy-27-methyl-24-oxa-cholecalciferol.

7. A pharmaceutical composition, comprising at least one compound according to claim 1 and a pharmaceutically compatible vehicle.

* * * * *